US010323222B2

(12) United States Patent
Curel et al.

(10) Patent No.: US 10,323,222 B2
(45) Date of Patent: Jun. 18, 2019

(54) DEVICE FOR AUTOMATED SEEDING OF CULTURE MEDIUM

(71) Applicant: INTELLIGENCE ARTIFICIELLE APPLICATIONS, Montpellier (FR)

(72) Inventors: Christian Curel, Laverune (FR); Michel Roch, Saint Bres (FR); Jean-Louis Cariou, Aubais (FR)

(73) Assignee: INTELLIGENCE ARTIFICIELLE APPLICATIONS, Montpellier (FR)

( * ) Notice: Subject to any disclaimer, the term of this patent is extended or adjusted under 35 U.S.C. 154(b) by 614 days.

(21) Appl. No.: 14/891,517

(22) PCT Filed: May 20, 2014

(86) PCT No.: PCT/FR2014/051170
§ 371 (c)(1),
(2) Date: Nov. 16, 2015

(87) PCT Pub. No.: WO2014/188113
PCT Pub. Date: Nov. 27, 2014

(65) Prior Publication Data
US 2016/0075986 A1    Mar. 17, 2016

(30) Foreign Application Priority Data

May 24, 2013    (FR) .................................... 13 54705

(51) Int. Cl.
*C12M 1/30* (2006.01)
*C12M 3/00* (2006.01)
(Continued)

(52) U.S. Cl.
CPC ............ *C12M 23/48* (2013.01); *C12M 33/00* (2013.01); *C12M 33/02* (2013.01); *C12M 41/48* (2013.01); *C12Q 1/24* (2013.01)

(58) Field of Classification Search
CPC .................................. C12M 33/02; C12Q 1/24
See application file for complete search history.

(56) References Cited

U.S. PATENT DOCUMENTS 3,850,754 A    11/1974  Wilkins et al.
4,144,135 A    3/1979   Sequeira
(Continued)

OTHER PUBLICATIONS

Search Report dated 2014.

*Primary Examiner* — Jonathan M Hurst
(74) *Attorney, Agent, or Firm* — Ipsilon USA, LLP

(57) ABSTRACT

The invention relates to a device (1) for automated inoculation of a culture medium, the device being of the type comprising:
  a clamp (2) suitable for gripping the inoculation tool;
  a clamp-holder (3);
  a support base (4) carrying the assembly formed by the clamp (2) and the clamp-holder (3); and
  a support structure (5) for supporting the support base (4) and for enabling the support base (4) to be moved along three axes.

The device is characterized in that the assembly formed by the clamp (2) and the clamp-holder (3) is an assembly mounted to move in pivoting in such a manner that it is tiltable relative to the support base (4), in that the clamp (2) is fitted with pivot branches (6) mounted to pivot between two positions, one being an open position and the other being a closed position, pivoting being driven by drive means (7) preferably acting on return means (8), and in that the clamp (2) is a rotary clamp mounted to revolve about an axis (BB') that is transverse and preferably orthogonal to the pivot axis (AA') of the branches (6) of the clamp (2).

11 Claims, 6 Drawing Sheets

(51) Int. Cl.
  *C12M 1/26* (2006.01)
  *C12M 1/36* (2006.01)
  *C12Q 1/24* (2006.01)

(56) References Cited

U.S. PATENT DOCUMENTS

| | | |
|---|---|---|
| 5,206,171 A | 4/1993 | Dillon et al. |
| 6,617,146 B1 | 9/2003 | Naccarato et al. |
| 2007/0202564 A1* | 8/2007 | Glasson ................ C12M 33/02 435/30 |
| 2013/0017127 A1 | 1/2013 | Tokumaru |

\* cited by examiner

DEVICE FOR AUTOMATED SEEDING OF CULTURE MEDIUM

RELATED APPLICATIONS

This application is a National Phase Application of PCT/FR2014/051170, filed on May 20, 2014, which in turn claims the benefit of priority from French Patent Application No. 13 54705 filed on May 24, 2013, the entirety of which are incorporated herein by reference.

BACKGROUND

Field of the Invention

The present invention relates to a device for automated inoculation of a culture medium.

Description of Related Art

There exist several tools for inoculation such as the inoculator loop, the Drigalski spatula, and swabs, certain tools being suitable for being secured to a stopper closing the container containing the culture medium to be inoculated.

Until now, inoculation has taken place essentially manually. For automated inoculation, inoculators are dedicated to only one type of inoculation tool, which thus limits their use, as shown for example in Document US 2013/0017127 in which the inoculation tool is formed by an injection syringe.

In Document WO 92/11538 the inoculation device includes a horizontal branch carrying gripper means at one of its ends. However, even those gripper means cannot grip an inoculation tool coupled to a stopper that is itself screwed into a support, such as a test tube, housing said inoculation tool, when the stopper on said support is in the screwed-in state.

OBJECTS AND SUMMARY

An object of the present invention is to provide an inoculation device of the above-mentioned type, of design that enables several types of inoculation tool to be used for inoculating in automated manner, including when the tool is secured to a stopper for closing the container containing said culture medium, said stopper being screwed into the container.

The invention provides a device for automated inoculation of a culture medium, the device being of the type comprising:
- a clamp suitable for gripping the inoculation tool;
- a clamp-holder;
- a support base carrying the assembly formed by the clamp and the clamp-holder; and
- a support structure for supporting the support base and for enabling the support base to be moved along three axes, the device being characterized in that the assembly formed by the clamp and the clamp-holder is an assembly mounted to move in pivoting in such a manner that it is tiltable relative to the support base, in that the clamp is fitted with pivot branches mounted to pivot between two positions, one being an open position and the other being a closed position, pivoting being driven by drive means preferably acting on return means, and in that the clamp is a rotary clamp mounted to revolve about an axis that is transverse and preferably orthogonal to the pivot axis of the branches of the clamp.

The presence of a clamp with pivot branches makes it possible to grip any type of tool. The ability of the clamp to revolve makes it possible both to grip an inoculation tool that is secured to a stopper screwed into its support by means of said stopper, and, by the clamp revolving, to unscrew the stopper from its support that is prevented from rotating, e.g. by co-operating with a support-holder. The tilting of the clamp and clamp-holder assembly relative to the support base that is itself mounted to move along three axes X, Y, Z that are preferably mutually orthogonal makes it possible to reproduce the manual gesture of an operator who tilts the inoculation tool and who makes a plurality of lines on the surface of the medium to be inoculated with the tool in the tilted state.

For reasons of simplicity of construction and of use, the axis of rotation about which the clamp revolves and the tilt axis of the clamp and clamp-holder assembly are preferably substantially mutually orthogonal.

The term "substantially mutually orthogonal" means mutually orthogonal within 15°.

Preferably, when in the closed position corresponding to the close-together position of said branches, the clamp and its pivot arms form an elongate body and the axis about which the clamp is mounted to revolve is formed by the mean longitudinal axis of said body.

Preferably, the drive means for driving the branches of the clamp pivotally comprise at least one "linear" cam arranged between the branches of the clamp, and motor means for driving the cam axially along an axis that coincides with the axis of rotation of the clamp following a path during which the cam is suitable for pressing against said branches of the clamp, at least from time to time.

This configuration makes it possible to make the drive means more compact without impairing the accuracy with which the pivot stroke of the branches of the clamp is controlled.

Preferably, the motor means for driving the cam axially back and forth comprise a nut-and-leads crew-assembly, in which the screw, of axis that coincides with the axis of rotation of the clamp, holds the cam, and in which the nut is axially stationary and is fitted with motor means for driving it in rotation.

Preferably, the cam is in the form of a tubular body engaged in such a manner as to rotate freely on the screw.

Mounting the cam to rotate freely on the screw makes it possible to rotate the clamp in all (open or closed) positions of said clamp.

Preferably, the outer peripheral portion of the cam, suitable for pressing against the branches of the clamp, is of generally conical shape.

In order to facilitate the pressing contact between the cam and the clamp and in order to avoid premature wear of the cam or the clamp, each branch of the clamp presents a bearing member in its zone that is suitable for pressing against the cam, which bearing member is of axis that is orthogonal to the axis of rotation of the clamp, and has its outer peripheral surface forming the surface of the branch of the clamp that is in pressing contact with the cam.

Preferably, each pivot branch of the clamp is formed by at least one two-armed pivot lever, having arms referred to respectively as a first arm and a second arm, the first arms forming between them the gripper zone of the clamp, tending to move apart from each other when the clamp passes from the closed position to the open position, the second arms being arranged on opposite sides of the cam.

In this embodiment, the conical outer peripheral portion of the cam forms a sloping ramp tending to move the second arms apart from each other by pressing against the second arms, during axial movement of the cam away from, the first arms towards the second arms.

The first arms of the two-armed levers are spaced apart from each other from their free ends towards the pivot axis of the lever by a distance that is not constant.

By means of this arrangement, for a predetermined spacing position, the first arms are suitable for exerting a varying clamping force that increases when the distance between the arms decreases. As a result, the first arms can grip a large number of inoculation tools.

Preferably, in the embodiment in which the drive means for driving the branches of the clamp pivotally comprise at least one "linear" cam, arranged between the branches of the clamp, and motor means for driving the cam axially along an axis that coincides with the axis of rotation of the clamp following a path during which the cam is suitable for being, at least from, time to time, pressed against said branches of the clamp, the return means are configured to return the clamp to the open position and the cam is mounted to move axially between the branches of the clamp going away from the clamping free ends of the clamp so as to pass the clamp from the open position to the closed position.

Preferably, in the embodiment in which the motor means for driving the cam axially back and forth comprise a nut-and-leadscrew assembly, in which the screw, of axis that coincides with the axis of rotation of the clamp, holds the cam, and in which the nut is axially stationary and is fitted with motor means for driving it in rotation, the device includes a presence sensor in the form of a rod on the same axis as the axis of rotation of the clamp, said rod, in the vertical position, being mounted to slide under the effect of its own weight inside the screw until it reaches an end-of-stroke position in which it projects from one end of the screw and extends between the branches of the clamp, and being-retractable into the screw merely by exerting thrust on the end of the rod that projects between said branches of the clamp.

The presence sensor is used in particular to detect the presence of a stopper.

BRIEF DESCRIPTION OF THE DRAWINGS

The invention can be better understood on reading the following description of embodiments, given with reference to the accompanying drawings, in which.

DETAILED DESCRIPTION

Figure 1:
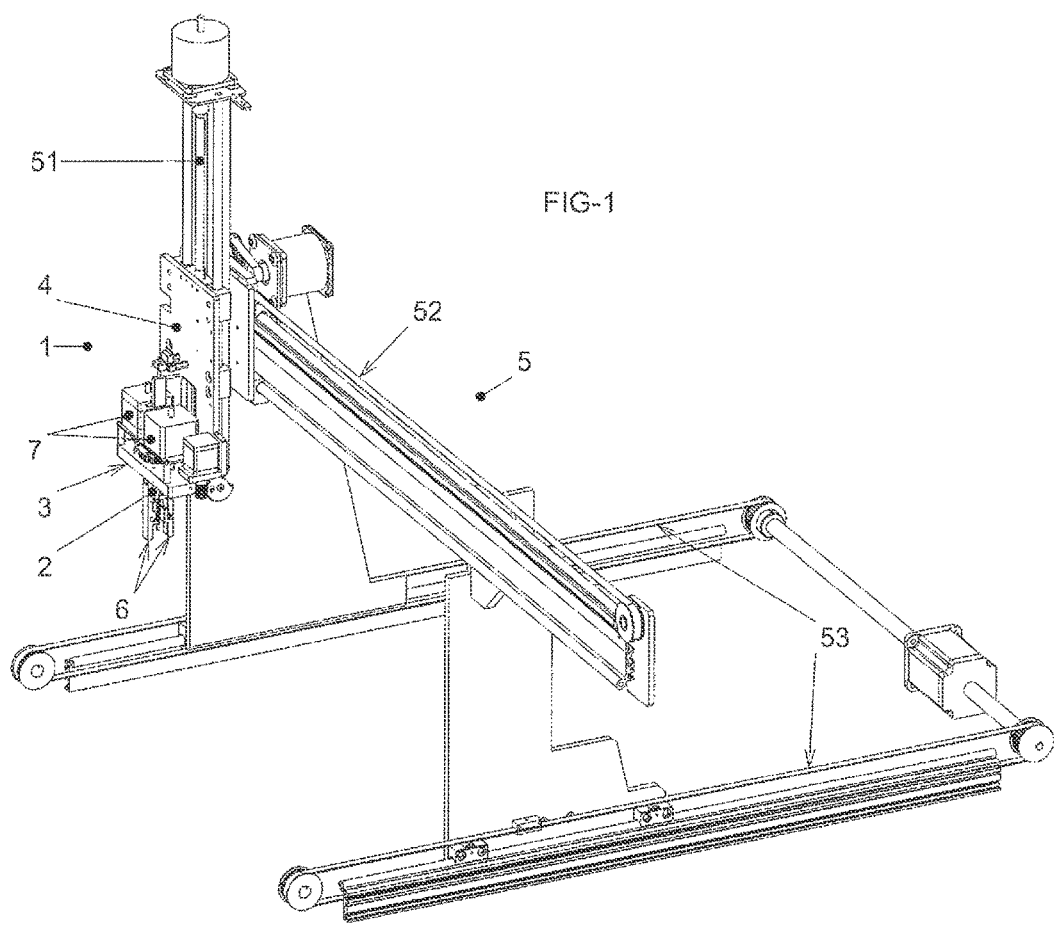
FIG. 1 is a perspective view of an installation of a device of the invention.
Figure 2:
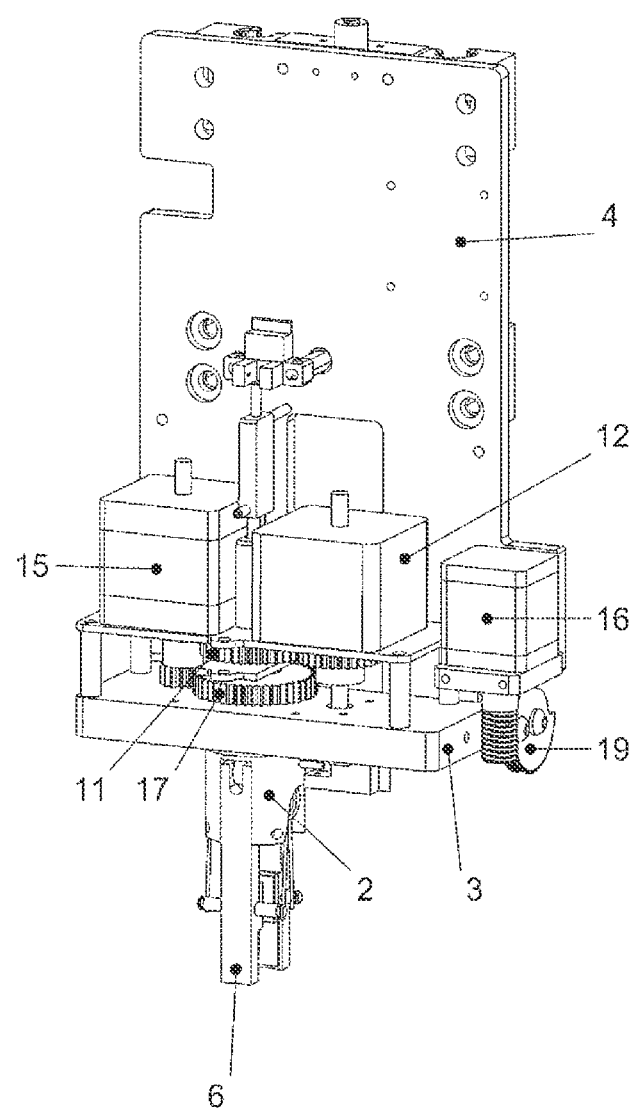
FIG. 2 is view of the clamp and clamp holder assembly mounted in a non-tilted position on a support base.

As mentioned above, the device 1 forming the subject matter of the invention is more particularly designed to enable inoculation to be automated.

This device is a general-purpose device designed for manipulating various inoculation tools such as a swab generally coupled with a stopper, a loop, a Drigalski spatula, and for inoculating various supports, such as a Petri dish or a microplate.

This device comprises:
- a clamp 2 suitable for gripping the inoculation tool;
- a clamp-holder 3;
- a support base 4 carrying the assembly formed by the clamp 2 and the clamp-holder 3; and
- a support structure 5 for supporting the support base 4 and for enabling the support base 4 to be moved along three axes.

The clamp 2 comprises a clamp body and branches 6, each mounted to pivot on said clamp body about a pivot axis AA'. In the example shown, each branch 6 of the clamp presents its own pivot axis AA', said pivot axes AA' being mutually parallel.

Furthermore, the clamp 2 is a rotary clamp mounted to revolve about a transverse axis BB', that is preferably orthogonal to the pivot axis AA' of the branches 6 of the clamp.

In the example shown, the clamp and its pivot branches, when in the closed position corresponding to the close-together position of said branches, form an elongate body, and the axis BB' about which the clamp is mounted to revolve is formed by the mean longitudinal axis of said body. The axis BB' about which the clamp is mounted to revolve, i.e. to rotate about its own axis, passes through the open space left between the pivot-branches 6 of the clamp 2 or the pivot axes of said branches. Mounting the clamp to revolve makes it possible for said clamp to grip an inoculation tool, such as a swab secured to a stopper that is screwed into a container, such as a test tube, e.g. containing a culture medium, said gripping taking place via said stopper. Revolving the clamp makes it possible to turn the stopper and its inoculation tool in order to unscrew the stopper from the test tube that is itself prevented from moving, e.g. by being force fitted in a tube-holder. Once the stopper has been unscrewed, the stopper and its inoculation tool can be handled like a conventional inoculation tool that is not secured to a stopper that is screwed into a container housing said inoculation tool. The clamp thus acts to turn the screw.

The device comprises drive means 7 for driving the branches of the clamp pivotally.

These drive means 7 for driving the branches 6 of the clamp 2 pivotally comprise at least one "linear" cam 9, arranged between the branches 6 of the clamp 2, and motor means 10, 11, 12, for driving the cam 9 axially along an axis that coincides with the axis of rotation BB' of the clamp 2 following a path during which the cam 9 is suitable for being pressed against said branches 6 of the clamp 2, at least from time to time.

These motor means 10, 11, 12 for driving the cam 9 axially back and forth comprise a nut-and-leadscrew assembly 11, 10, in which the screw 10, of axis that coincides with the axis of rotation BB' of the clamp 2, holds the cam 9, and in which the nut 11, which is axially stationary, is provided with motor means 12 for driving it in rotation.

These motor means 12 are in this example formed by a motor member meshing with the outer peripheral surface of the nut. Rotating the nut thus generates axial movement of the screw in a direction that depends on the direction of rotation of the nut.

The cam 9 is in the form of a tubular body engaged in such a manner as to rotate freely on the screw 10.

To this end, bearing members 18 are interposed between the cam 9 and the screw 6. These bearing members thus enable the clamp to be driven in rotation whatever the (opened or closed) position of said clamp.

In addition, the screw 6 is provided with an abutment for limiting axial movement of the cam along the screw, causing the cam to be constrained to move axially with the screw in at least one direction, and in the opposite direction, the cam is constrained to move axially with the screw by the effect of its own weight.

In its area suitable for coming to press against the cam 9, each branch 6 of the clamp 2 presents a bearing member 13 of axis that is orthogonal to the axis of rotation BB' of the clamp 2, and having its outer peripheral surface forming the surface of the branch 6 of the clamp 2 that presses against the cam 9.

In the examples shown, each pivot branch 6 of the clamp 2 is formed by at least one two-armed pivot lever 61, 62, with arms referred to as first and second arms, the first arms 61, which form between them, the gripper zone of the clamp 2, tending to move apart from each other when the clamp 2 passes from the closed position to the open position, and the second arms 62 being arranged on opposite sides of the cam 9.

The clamp is fitted with return means 8 acting on drive means 7 for driving the branches of the clamp pivotally. These return means 8 are formed by a hairpin spring with each branch of the pin being applied against a branch of the clamp.

The return means are configured to return a clamp 2 to the open position and the cam 9 is mounted to move axially between the branches 6 of the clamp 2 going away from the clamping free ends of the clamp 2 so as to pass the clamp 2 from the open position to the closed position by means of the cam acting on the second arms 62 of the branches of the clamp, which branches tend to move away from each other under the effect of each cam.

Figure 5:
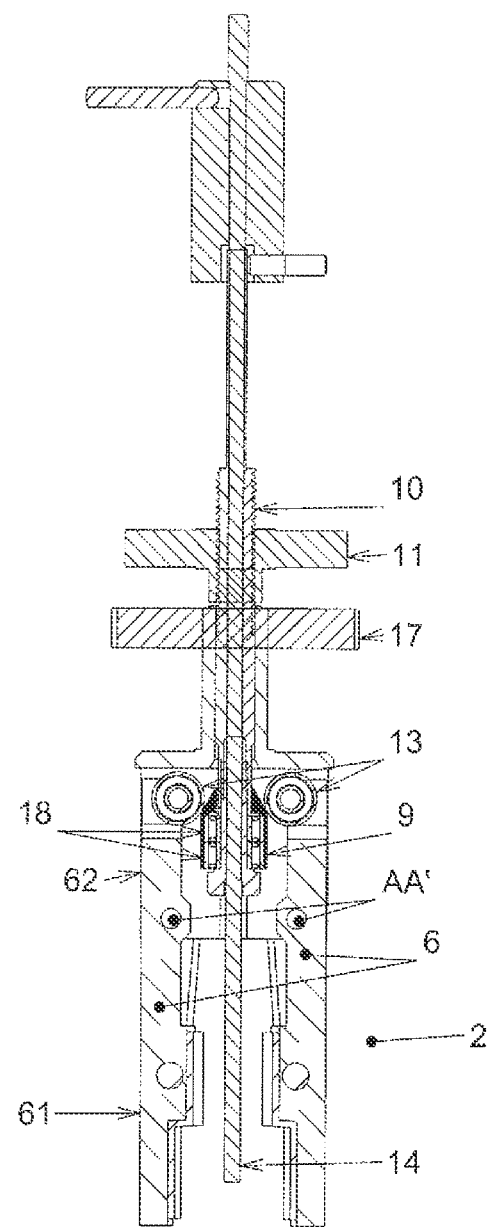
FIG. 5 is fragmentary section view of the clamp in a closed position of the clamp.
Figure 6:
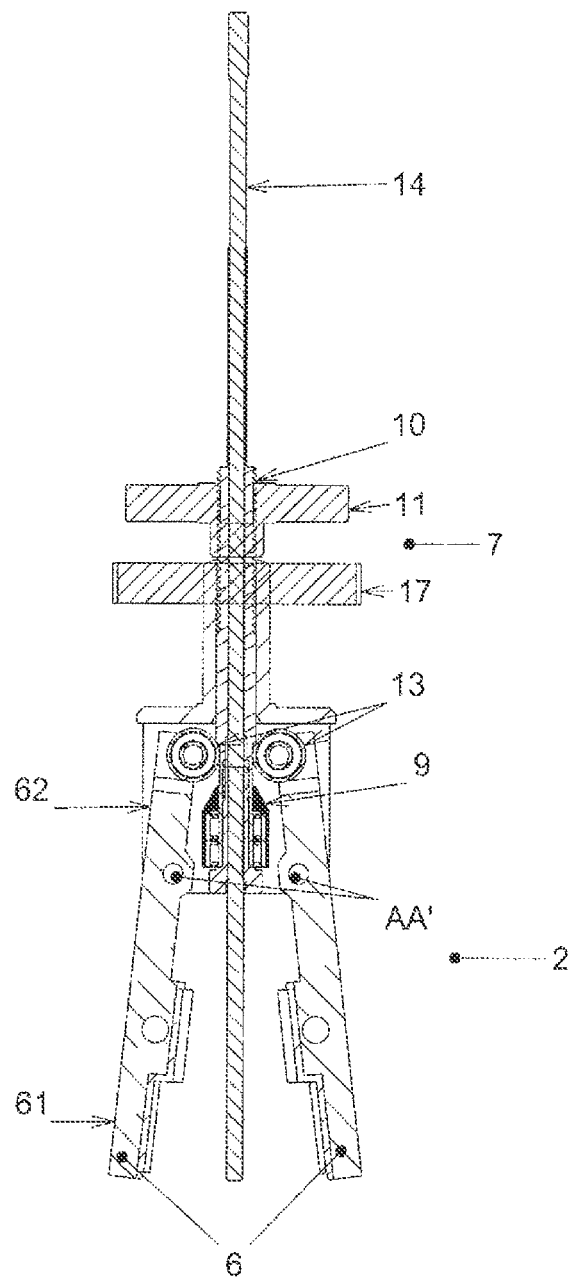
FIG. 6 is fragmentary section view of the clamp in an open position of the clamp.

The conical outer peripheral portion of the cam 9 forms a sloping ramp that, during axial movement of the cam 9 away from the first arms 61 towards the second arms 62, presses against the second arms 62, tending to move the second arms 62 apart from each other, and consequently generates movement of the first arms towards each other, which corresponds to the branches of the clamp passing from the open position to the closed position, as shown by the passage from FIG. 6 to FIG. 5.

During this movement, the cam comes to press against the bearing members 13 incorporated in the branches of the clamp, so as to reduce wear of the device.

In order to allow the clamp to pass from the closed position to the open position, it suffices to use the screw 10 to move the cam 9 axially in an opposite direction, i.e. away from the second arms 62 towards the first arms 61 of the branches of the clamp. During this movement, the cam 9 releases the space between the bearing members 13 of the clamp branches, so that, under the effect of the return means, the second arms are able to move closer to each other, this movement consequently causing the first arms to move apart, which movement corresponds to the clamp passing into the open position.

It should, be observed that in the examples shown, the first, arms 61 of the two-armed levers are spaced apart from each other from their free ends towards the pivot axes of the levers by a distance that is not constant.

In particular, in their mid-zones the first arms of the branches of the clamp are fitted on their facing faces with respective projecting portions that make it possible, for a given spacing of the branches, to grip objects of smaller size by using said projecting portions. These projecting portions are provided with a respective pads made of non-slip material such as an elastomer, in particular in order to facilitate screwing/unscrewing operations.

As mentioned above, the clamp 2 is a rotary clamp mounted to revolve about an axis BB' that is substantially orthogonal to the pivot axes AA' of the branches, said axis BB' extending at least in part in the space left free between the pivot axes AA' of the branches 6 of the clamp.

In order to cause the clamp to revolve, the device includes a motor 15 having its outlet shaft meshing with the clamp body in order to drive said body in rotation.

To this end, the clamp body 2 is fitted with a gear 17 shown in this example as being coaxial about the screw 10, said gear 17 engaging with the outlet shaft of the motor 15, directly or via at least one other gear.

The clamp 2 is carried by a clamp-holder 3, which in this example is in the form of a plate through which part of the body of the clamp projects. The branches of the clamp extend below said plate, while the motor means for rotating the nut and the clamp body are arranged above said plate and are carried thereby.

This clamp-holder plate 3 is itself mounted to pivot on the support base 4, in such a manner that the assembly formed by the clamp 2 and the clamp-holder 3 is an assembly mounted to pivot in such a manner that it is tiltable relative to the support base 4.

Figure 3:
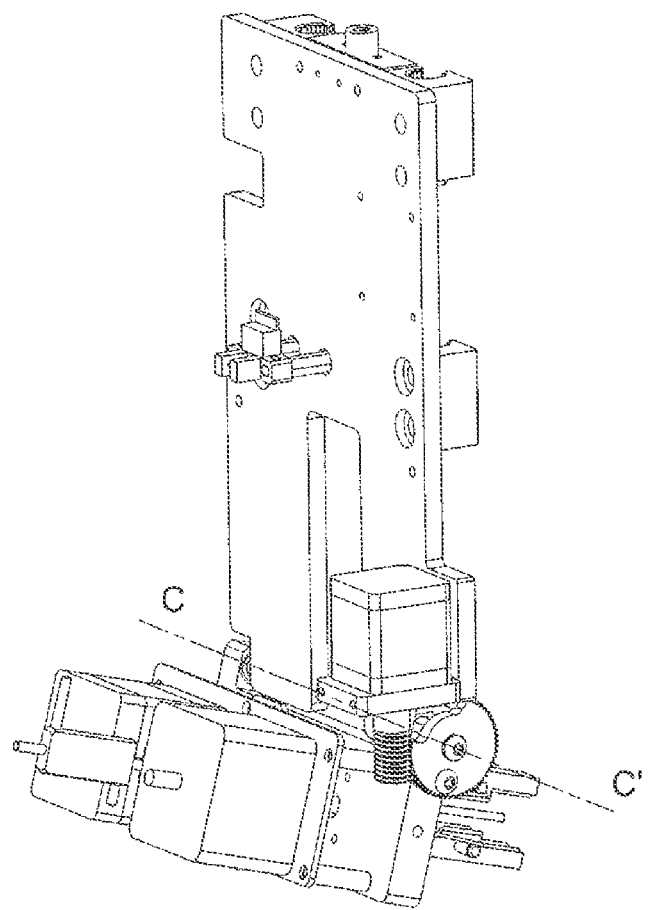
FIG. 3 is view of the clamp and clamp holder assembly mounted in a tilted position on a support base.
Figure 4:
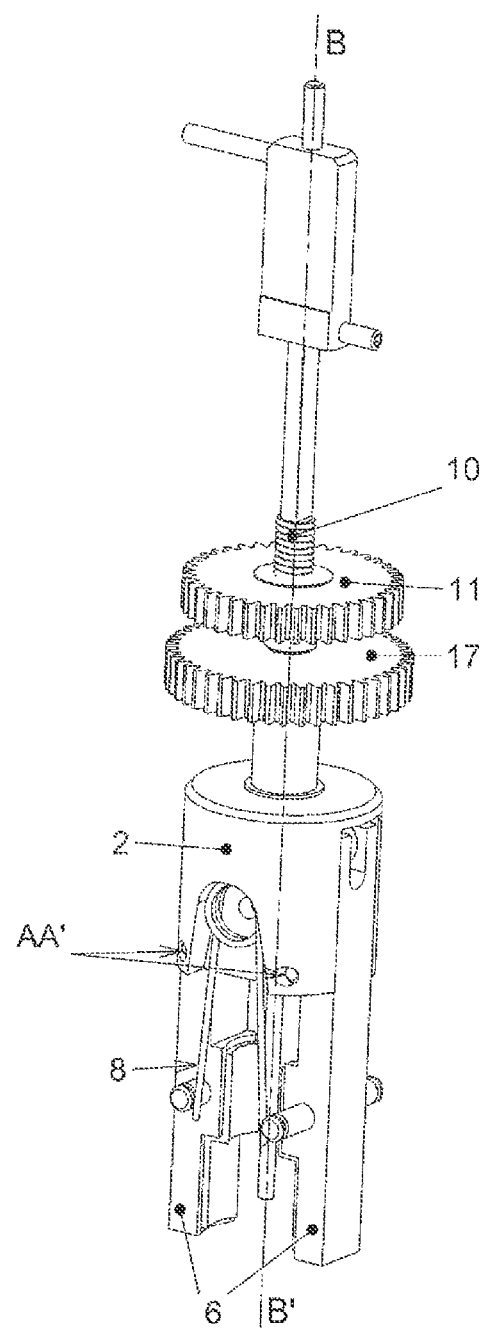
FIG. 4 is a fragmentary view in perspective of a clamp and of motor means for driving the branches of the clamp pivotally.

The pivot axis about which the clamp and clamp-holder assembly pivots is referenced CC' in FIG. 3.

It should be observed that the axis of rotation BB' about which the clamp 2 revolves and the tilt axis CC' of the clamp and clamp-holder assembly 2, 3 are substantially mutually orthogonal.

In order to control such tilting, a motor member 16 is arranged on the support base 4, and the outlet shaft of said motor member 16 forms a worm screw meshing with a toothed wheel 19 carried by the clamp-holder 3. This toothed wheel 19 is screw-fastened to the clamp-holder 3.

The support base 4 has the form of a plate mounted to move in sliding along a portion of the support structure 5. The support structure comprises three rails 51, 52, 53 that are mutually orthogonal. The support base 4 slides along the vertical rail 51 referred to as the "Z rail", itself sliding along the horizontal rail 52 referred to as the "Y rail", itself being suitable for moving in sliding along the horizontal rail 53 referred to as the "X rail".

By way of example, this combination of movements makes it possible to use an inoculation tool gripped by the clamp, tilted by pivoting the clamp and clamp-holder assembly, and moved using the support structure, in order to obtain a zigzag pattern on the surface of a Petri dish.

To finish off the device, there is provided a presence sensor 14 in the form of a rod on the same axis as the axis of rotation BB' of the clamp. This rod is in a vertical position, mounted to move under the effect of its own weight by sliding inside the screw 10 until it reaches an end-of-stroke position in which it projects from one end of the screw and extends between the branches 6 of the clamp. This rod, which is mounted in this way to be free in sliding inside the screw, is retractable by returning partially into the screw 10, merely by thrust being exerted on the end of the rod that is projecting between the branches 6 of the clamp. By way of example, this thrust is exerted when the clamp is brought above a tube fitted with a stopper to be gripped. By means of its free end arranged between the branches of the clamp, the rod then comes into contact with the stopper and returns into the screw. This axial movement of the rod can be detected using a sensor arranged at the end of the rod opposite from its end that projects between the branches of the clamp. The axial movement of the rod represents the fact that a stopper is present on the tube and that a stopper removal operation is going to be needed, e.g. an unscrewing operation.

In the examples shown, the detection sensor for detecting axial movement of the rod is shown by a unit that is carried by the clamp-holder and through which the rod passes. This unit can also form part of the detection means for detecting axial movement of the screw, said means contributing to controlling movement of the screw. At its end opposite the end that is suitable for projecting between the branches of the clamp, the rod is provided with a bulge that forms the end-of-stroke abutment for sliding movement of the rod. To this end, the bulge comes to press against the unit in the position in which the rod is projecting between the branches of the clamp.

The invention claimed is:

1. A device for automated inoculation of a culture medium, the device comprising:
   a clamp suitable for gripping an inoculation tool;
   a clamp-holder;
   a support base carrying the assembly formed by the clamp and the clamp-holder; and
   a support structure for supporting the support base and for enabling the support base to be moved along three axes;
   wherein an assembly formed by the clamp and the clamp-holder is an assembly mounted to move in pivoting about an axis (CC') in such a manner that it is tiltable relative to the support base, in that the clamp is fitted with pivot branches mounted to pivot between two positions, one being an open position and the other being a closed position, pivoting being driven by drive means preferably acting against return means, and in that the clamp is a rotary clamp mounted to revolve about an axis (BB') that is transverse and preferably orthogonal to a pivot axis (AA') of the branches of the clamp,
   wherein the drive means for driving the branches of the clamp pivotally comprise at least one "linear" cam arranged between the branches of the clamp, and motor means for driving the cam axially along an axis that coincides with the axis (BB') of the clamp following a path during which the cam is suitable for pressing against said branches of the clamp, at least from time to time.

2. A device according to claim 1, wherein the axis (BB') about which the clamp revolves and a tilt axis (CC') of the clamp and clamp-holder assembly are substantially mutually orthogonal.

3. A device according to claim 1, the motor means for driving the cam axially back and forth comprise a nut-and-leadscrew assembly, in which a leadscrew, of axis that coincides with the axis (BB') of the clamp, holds the cam and in which the nut is axially stationary and is fitted with motor means for driving it in rotation.

4. A device according to claim 3, the cam is in the form of a tubular body engaged in such a manner as to rotate freely on the leadscrew.

5. A device according to claim 1, wherein an outer peripheral portion of the cam, suitable for pressing against the branches of the clamp, is of generally conical shape.

6. A device according to claim 1, wherein each branch of the clamp presents a bearing member in its area suitable for pressing against the cam, which bearing member is of axis that is orthogonal to the axis of rotation (BB') of the clamp, and has its outer peripheral surface forming a surface of the branch of the clamp that is pressing against the cam.

7. A device according to claim 1, wherein each pivot branch of the clamp is formed by at least one two-armed pivot lever, having arms referred to respectively as a first arm and a second arm, first arms, forming between them a gripper zone of the clamp tending to move apart from each other when the clamp passes from the closed position to the open position, second arms being arranged on opposite sides of the cam.

8. A device according to claim 7,
   wherein the outer peripheral portion of the cam, suitable for pressing against the branches of the clamp, is of generally conical shape, and wherein
   the conical outer peripheral portion of the cam forms a sloping ramp tending to move the second arms apart from each other by pressing against the second arms during axial movement of the cam away from the first arms towards the second arms.

9. A device according to claim 7, wherein the first arms of the two-armed levers are spaced apart from each other from their free ends towards a pivot axis of the lever by a distance that is not constant.

10. A device according to claim 1 wherein the return means are configured to return the clamp to the open position and in that the cam is mounted to move axially between the branches of the clamp going away from clamping free ends of the clamp so as to pass the clamp from the open position to the closed position.

11. A device according to claim 3, wherein said device includes a presence sensor in the form of a rod on the same axis as the axis of rotation (BB') of the clamp, said rod in the vertical position, being mounted to slide under the effect of its own weight inside the screw until it reaches an end-of-stroke position in which it projects from one end of the leadscrew and extends between the branches of the clamp, and being retractable into the screw merely by exerting thrust on an end of the rod that projects between said branches of the clamp.

* * * * *